| United States Patent [19] | [11] Patent Number: 4,746,662 |
| Kerwar et al. | [45] Date of Patent: May 24, 1988 |

[54] TREATMENT OF ARTHRITIS WITH 3,5-DICHLOROMETHOTREXATE

[75] Inventors: Suresh S. Kerwar, Ossining; Adolph E. Sloboda, New City, both of N.Y.

[73] Assignee: American Cyanamid Company, Stamford, Conn.

[21] Appl. No.: 17,286

[22] Filed: Feb. 20, 1987

[51] Int. Cl.$^4$ .......................................... A61U 31/505
[52] U.S. Cl. ................................................. 514/258
[58] Field of Search ........................................ 514/258

[56] References Cited

U.S. PATENT DOCUMENTS 4,426,384  1/1984  Wyburn-Mason .................. 514/258

OTHER PUBLICATIONS

See-Lasley et al., Manual of Oncology Therapeutics (1981), pp. 228–229.

Chem. Abst., 99 (1983), 115, 669m.

*Primary Examiner*—Stanley J. Friedman
*Attorney, Agent, or Firm*—R. P. Raymond

[57] ABSTRACT

Joint destruction associated with arthritic disease in warm blooded animals is treated with unexpected safety using 3,5-dichloromethotrexate. The therapeutic index therefor is unexpectedly enhanced through combination therapy using a post administration of leucovorin.

4 Claims, No Drawings

TREATMENT OF ARTHRITIS WITH 3,5-DICHLOROMETHOTREXATE

The present invention relates to the treatment of rheumatoid arthritis and progressive joint deterioration with a certain pteridine compound and compositions useful therefor. Substituted pteridines which are structurally related to folic acid but are in fact folic acid antagonists in the animal body are taught in U.S. Pat. Nos. 2,512,572 and 2,570,391. U.S. Pat. No. 4,080,325 concerns a multi-step process useful in preparing such compounds.

The compound used in the practice of the present invention is N-{3,5-dichloro-4-[(2,4-diamino-6-pteridyl-methyl)methylamino]benzoyl}glutamic acid which is also known as 3,5-dichloromethotrexate and has the following structural formula:

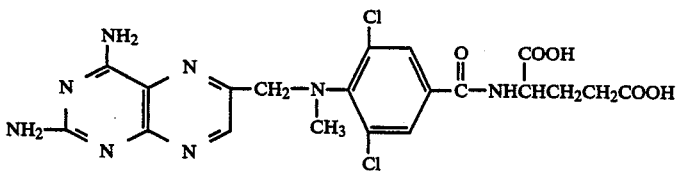

This compound can be prepared from known starting materials by the procedure of Example 24 of U.S. Pat. No. 2,570,391 in which it is described by the alternate name of 3',5'-dichloro-4-amino-1-methylpteroylglutamic acid.

Methotrexate, the corresponding deschloro analog, is described in U.S. Pat. No. 2,512,572. It has been sold for many years as an antineoplastic agent and for the treatment of psoriasis. For several years physicians have been treating patients having rheumatoid arthritis with methotrexate generally administered in low doses.

Methotrexate is an antimetabolite which should be administered by physicians experienced in antimetabolite chemotherapy because of the possibility of fatal or severe toxic reactions. Deaths have been reported in the use of methotrexate in the treatment of psoriasis. In the treatment of neoplastic diseases, some physicians administer methotrexate in very high dosages and rescue the patients by subsequent administration of leucovorin.

Methotrexate may produce marked depression of bone marrow, anemia, leukopenia, thrombocytopenia and bleeding. Diarrhea and ulcerative stomatitis are frequent toxic effects and require interruption of therapy; otherwise, hemorrhagic enteritis and death from intestinal perforation may occur.

Often structural modifications which lead to compounds having reduced levels of efficacy in treating the disease in question. Reducing toxicity is especially important in securing approval of products for the treatment of diseases which are not life threatening. Accordingly in the treatment of psoriasis, methotrexate is not recommended except in the case of severe, recalcitrant, disabling, psoriasis which is not adequately responsive to other forms of therapy.

Accordingly, it is an object of the present invention to provide a method of treating arthritis with a reduction in toxicity without sacrificing the level of efficacy hithertofore available with the use of methotrexate.

DESCRIPTION OF THE INVENTION

It has not been found that the inflammation and joint destruction associated with arthritic disease in warm-blooded animals can be suppressed with unexpected safety by using 3,5-dichloromethotrexate. The therapeutic index (LD50/ED50) is used to compare 3,5-dichloromethotrexate with methotrexate in the examples below. A higher therapeutic index indicates a greater margin of safety. It has further been found that the margin of safety (therapeutic index) in the treatment of arthritis with 3,5-dichloromethotrexate is unexpectedly enhanced through the post administration of leucovorin in comparison to the combination therapy with methotrexate.

The effectiveness and increased margin of safety associated with treatment with 3,5-dichloromethotrexate was established by the following tests.

Induction of Adjuvant Arthritis

Outbred, male, Royalhart Wistar rats (Royalhart Farms, New Hampton, NY), weighing approximately 165 g, were injected intradermally in the right hind paw with killed and dried Mycobacterium tuberculosis emulsified in mineral oil (adjuvant) at a dose of 2 mg/kg of body weight. This protocol for induction of arthritis has been described in detail by A. E. Sloboda and A. C. Osterberg, Inflammation, 1, 415 (1976).

Subsequent to immunization with the adjuvant, the rats were divided into several groups. Some groups of rats were treated daily by gavage with various doses of methotrexate or 3,5-dichloromethotrexate. Other groups were treated in the same manner, but two hours later these rats were also treated with an intraperitoneal dose of calcium leucovorin at 0.5 mg/kg of body weight. Control groups of rats were immunized with adjuvant, but then treated only with starch vehicle.

At the end of 23 days post adjuvant immunization, the left hind paw diameters of all the rats were measured around the ankle joint with a vernier caliper.

All of the control rats developed arthritis and on day 23 their average left hind paw diameter was approximately 11.9 mm.

The average left hind paw diameter of normal (non-immunized, non-treated) rats of the same age was 7.7 mm and over 95% of these normal rats had a left hind paw diameter of less than 8.2 mm. Therefore, immunized rats with a left hind paw diameter of 8.2 mm or greater were considered to be arthritic.

The results of this test are shown in Table I, wherein the LD50 is defined as the dose in mg/kg of body weight that is lethal to 50% of the rats and the ED50 is defined as the dose in mg/kg that completely suppresses the arthritis in 50% of the rats (i.e. the left hind paw diameter is less than 8.2 mm). The LD50 and the ED50 were derived by the statistical method of Litchfield and Wilcoxon, J. Pharmacol. Exp. Ther., 96, 99 (1949). The therapeutic index=LD50/ED50.

TABLE I

Therapeutic Index for Methotrexate and 3,5-Dichloromethotrexate in the Treatment of Adjuvant Arthritis

| Treatment | Daily Dose mg/kg | Dead/Treated | Percent Mortality | Mean LD50 mg/kg | No* of Rats With Arthritis No. Survivors | Percent with Arthritis | Mean ED50 mg/kg | Therapeutic Index (LD50/ED50) |
|---|---|---|---|---|---|---|---|---|
| Methotrexate | 0.25 | 16/18 | 88.9 | 0.133 (0.099–0.180)** | 0/2 | 0.0 | 0.100 (0.071–0.140)** | 1.33 |
|  | 0.125 | 10/27 | 37.0 |  | 3/17 | 17.6 |  |  |
|  | 0.063 | 1/18 | 5.6 |  | 12/17 | 70.5 |  |  |
|  | 0.031 | 1/18 | 5.6 |  | 15/16 | 93.8 |  |  |
| 3,5-Dichloromethotrexate | 6.25 | 23/27 | 85.2 | 3.13 (2.34–4.19)** | 0/4 | 0.0 | 0.79 (0.45–1.37)** | 3.96 |
|  | 3.13 | 15/27 | 55.5 |  | 0/12 | 0.0 |  |  |
|  | 1.57 | 2/18 | 11.1 |  | 6/16 | 37.5 |  |  |
|  | 0.79 | 2/18 | 11.1 |  | 5/16 | 31.3 |  |  |
|  | 0.39 | 0/9 | 0.0 |  | 8/9 | 88.9 |  |  |
| Methotrexate followed 2 hours later by 0.5 mg/kg calcium leucovorin | 0.25 | 5/9 | 55.6 | 0.235 (0.147–0.383)** | 1/4 | 25.0 | 0.136 (0.080–0.231)** | 1.73 |
|  | 0.125 | 3/18 | 16.7 |  | 7/15 | 46.7 |  |  |
|  | 0.063 | 0/9 | 0.0 |  | 8/9 | 88.9 |  |  |
|  | 0.031 | 0/9 | 0.0 |  | 9/9 | 100.0 |  |  |
| 3,5-Dichloromethotrexate followed 2 hours later by 0.5 mg/kg calcium leucovorin | 6.25 | 6/18 | 33.3 | 9.0 (5.2–15.5)** | 1/12 | 8.3 | 1.37 (0.087–2.15)** | 6.57 |
|  | 3.13 | 0/18 | 0.0 |  | 2/18 | 11.1 |  |  |
|  | 1.57 | 1/9 | 11.1 |  | 2/8 | 25.0 |  |  |
|  | 0.79 | 0/9 | 0.0 |  | 9/9 | 100.0 |  |  |
|  | 0.39 | 0/9 | 0.0 |  | 9/9 | 100.0 |  |  |

*Number of surviving rats with left hind paw diameter of 8.2 mm or greater.
**Values in parentheses represent range in mg/kg of body weight.

The results in Table I show that the ED50 for methotrexate is 0.1 mg/kg and the ED50 for 3,5-dichloromethotrexate is 0.79 mg/kg, indicating that 3,5-dichloromethotrexate is approximately eight times less efficacious than methotrexate. However, the LD50 for methotrexate is 0.133 mg/kg and the LD50 for 3,5-dichloromethotrexate is 3.13 mg/kg, indicating that 3,5-dichloromethotrexate is approximately 24 times less toxic than methotrexate.

The therapeutic index (LD50/ED50) for methotrexate is 1.33 and for 3,5-dichloromethotrexate is 3.96, indicating that treatment with 3,5-dichloromethotrexate provides a three fold increased margin of safety.

The results in Table I also show that the margin of safety associated with 3,5-dichloromethotrexate treatment can be further increased by added treatment with calcium leucovorin as indicated by an increase in the therapeutic index from 3.96 to 6.57. In contrast the therapeutic index with methotrexate and calcium leucovorin treatment is only marginally increased from 1.33 to 1.73.

These results show that 3,5-dichloromethotrexate is safer than methotrexate in the treatment of adjuvant arthritis and the safety of 3,5-dichloromethotrexate can be further improved by calcium leucovorin when administered two hours post 3,5-dichloromethotrexate treatment.

This increased margin of safety in terms of inhibition of progressive joint deterioration was also demonstrated by the following test.

Inhibition of Progressive Joint Destruction

In separate experiments, rats were injected intradermally in the right hind paw with killed and dried Mycobacterium tuberculosis emulsified in mineral oil (adjuvant) at a dose of 2 mg/kg of body weight. These rats were divided into several groups. Some groups of rats were treated daily by gavage with various doses of methotrexate or 3,5-dichloromethotrexate. Other groups were treated in the same manner, but two hours later these rats were also treated with an intraperitoneal dose of calcium leucovorin at 0.5 mg/kg of body weight. This protocol is identical to the experiment whose results are described in Table I. At the end of 23 days the rats were killed, their left hind paws amputated and radiographic evaluation was made as follows: Joint roentgraphs of the left hind paws were prepared on Polaroid x-ray film (type 55) using a Faxitron x-ray unit (Model 43805-N, Hewlett Packard, McMinnville, OR). The focus to film distance was 45 cm and the exposure to the x-ray source was 5 minutes at 60 KVP. Each radiograph was graded (blind) for the presence and severity of the following parameters:

(a) bone mineralization-osteoporosis in the calcaneus;
(b) justaarticular erosions of the tarsal bones;
(c) periostitis-subperiosteal new bone formation involving the distal tarsal bones and the distal tibia;
(d) cartilage space narrowing; and
(e) erosions of joint alignment in the distal phalanges.

A grade of 0 to 4 (with 0=normal and 4=severe changes) was assigned to each of the five parameters. The total score was the sum of the individual scores and represented the overall joint destruction of the left hind paw.

The total overall joint destruction score for arthritic controls was 16.2. For the purpose of calculating the percent of treated rats showing x-ray improvement, all individual rats with a total score of 8 or less were considered to show an improvement of x-ray parameters (significantly less joint destruction). The percentage of rats with improved total x-ray scores was determined and the ED50 was calculated. A therapeutic index (LD50/ED50) based on the relationship of drug induced mortality shown in the previous experiments and drug induced effects on these radiographic parameters was calculated. The results are shown in Table II.

TABLE II

Therapeutic Index for Methotrexate and 3,5-Dichloromethotrexate in the Inhibition of Arthritis Induced Joint Deterioration

| Treatment | Daily Dose mg/kg | No. of Rats With Improved X-Ray Score n | Percent with Improved Scores | Mean ED50 mg/kg | X-Ray Therapeutic Index** ($\frac{LD50}{ED50}$) |
|---|---|---|---|---|---|
| Methotrexate | 0.125 | 11/11 | 100.0 | 0.071 (0.061–0.082)* | 1.87 |
|  | 0.063 | 3/18 | 10.7 |  |  |
|  | 0.031 | 0/15 | 0.0 |  |  |
| 3,5-Dichloro-methotrexate | 3.13 | 10/11 | 90.0 | 0.75 (0.54–1.05)* | 4.17 |
|  | 1.57 | 14/16 | 87.5 |  |  |
|  | 0.79 | 12/17 | 70.6 |  |  |
|  | 0.39 | 3/18 | 16.7 |  |  |
| Methotrexate followed 2 hours later by 0.5 mg/kg calcium leucovorin | 0.125 | 8/15 | 53.3 | 0.120 (0.098–0.148)* | 1.96 |
|  | 0.063 | 0/18 | 0.0 |  |  |
|  | 0.031 | 0/16 | 0.0 |  |  |
| 3,5-Dichloromethotrexate followed 2 hours later by 0.5 mg/kg calcium leucovorin | 6.25 | 9/9 | 100.0 | 1.02 (0.82–1.28)* | 8.82 |
|  | 3.13 | 16/16 | 100.0 |  |  |
|  | 1.57 | 11/17 | 64.7 |  |  |
|  | 0.79 | 8/17 | 47.0 |  |  |
|  | 0.39 | 0/18 | 0.0 |  |  |

*Values in parentheses represent range in mg/kg of body weight.
**Therapeutic index calculated using LD50 from previous experiments (see Table I).

The results in Table II show that 3,5-dichloromethotrexate has an improved therapeutic index over methotrexate in respect to drug effects on arthritis induced joint destruction.

Administration of calcium leucovorin 2 hours post-treatment to rats treated with either methotrexate or 3,5-dichloromethotrexate improves the therapeutic index for both compounds.

The combination of 3,5-dichloromethotrexate and calcium leucovorin produced in the greatest improvement in the therapeutic index.

3,5-Dichloromethotrexate has proven safe and effective in treating arthritis and inhibiting joint deterioration in mammals when administered in amounts ranging from about 0.10 mg to about 6.0 mg per kg of body weight would be from about 1.0 mg to about 3.0 mg per kg of body weight per day, and such units are employed that a total of from about 50.0 mg to about 150.0 mg of 3,5-dichloromethotrexate, for a subject of about 70 kg of body weight weight are administered in a 7 day period.

This dosage regimen may be adjusted to provide the optimum therapeutic response. For example, several divided doses may be administered daily, or the dose may be proportionally reduced as indicated by the exigencies of the therapeutic situation.

3,5-Dichloromethotrexate may be administered orally or parenterally, with oral administration preferred.

3,5-Dichloromethtrexate may be orally administered, for example, with an inert diluent or with an assimilable edible carrier, or it may be enclosed in hard or soft shell gelatin capsules, or it may be compressed into tablets, or it may be incorporated with the food of the diet.

For oral therapeutic administration 3,5-dichloromethotrexate may be incorporated with excipients and used in the form of tablets, capsules, elixirs, suspensions, syrups and the like. Such compositions and preparations should contain at least 0.1% of 3,5-dichloromethotrexate. The percentage of 3,5-dichloromethotrexate in these preparations may vary and may conveniently be between 2% and 60% of the weight of the unit. The percentage of 3,5-dichloromethotrexate in such therapeutically useful compositions is such that a suitable dosage will be obtained.

The tablets, capsules and the like may also contain a binder such as gum tragacanth, acacia or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added, or a flavoring agent such as peppermint, oil of wintergreen, or cherry flavoring.

When the dosage unit form is a capsule, it may contain, in addition to materials of the above type, a liquid carrier such as a fatty oil.

Various other materials may be present as coatings or to otherwise modify the physical form of the dosage unit. For instance, tablets or capsules may be coated with shellac, sugar or both. A syrup or elixir may contain sucrose, methyl and propylparabens as preservatives, a dye and flavoring such as cherry or orange flavor. Any material used in preparing any dosage unit form must be pharmaceutically pure and substantially non-toxic in the amounts employed.

For parenteral administration, the 3,5-dichloromethotrexate should be employed as a pharmaceutically acceptable salt such as the sodium salt.

Leucovorin (folinic acid) is conventionally administered by intramuscular injection as an aqueous solution of the calcium salt. It is preferably administered within 1 to 2 hours of the 3,5-dichloromethotrexate using from 1 to 2 mg of the calcium leucovorin reconstituted for aqueous injection.

Other embodiments of this invention will be obvious to those skilled in the art without departing from the spirit thereof.

We claim:
1. A method for the treatment of arthritis and progressive joint deterioration characterized by administering an effective amount of N-{3,5-dichloro-4-[(2,4- diamino-6-pteridylmethyl)methylamino]benzoyl}
glutamic acid or a pharmaceutically acceptable salt thereof to a patient having such conditions.

2. A method according to claim 1 wherein the therapeutic index is substantially increased by the post administration of calcium leucovorin.

3. A method according to claim 2 wherein adjuvant arthritis is treated with 3,5-dichloromethotrexate and the therapeutic index is about 6.

4. A method according to claim 1 wherein the active ingredient is 3,5-dichloromethotrexate and the preferred dosage regimen is from 1 to 3 mg per kg of body weight per day.

* * * * *